United States Patent [19]

Mcvie et al.

[11] Patent Number: 5,397,824
[45] Date of Patent: Mar. 14, 1995

[54] ORGANOSILICON COMPOUNDS AND THEIR USE IN FILM-FORMING COMPOSITIONS

[75] Inventors: James Mcvie, Barry; Martin Rowlands, Neath, both of Wales

[73] Assignee: Dow Corning Limited, Barry, United Kingdom

[21] Appl. No.: 51,417

[22] Filed: Apr. 23, 1993

Related U.S. Application Data

[62] Division of Ser. No. 844,090, Mar. 2, 1992, Pat. No. 5,246,996.

[30] Foreign Application Priority Data

Mar. 14, 1991 [GB] United Kingdom ............... 9105371

[51] Int. Cl.$^6$ .............................................. C08K 5/54
[52] U.S. Cl. .................................... 524/265; 524/590; 556/445; 427/387; 525/453
[58] Field of Search ............... 556/445; 524/265, 590; 525/457; 427/387

[56] References Cited

U.S. PATENT DOCUMENTS

| 3,384,599 | 5/1968 | Omietanski et al. | 528/28 |
| 3,887,601 | 6/1975 | Kanner et al. | 556/445 |
| 4,052,495 | 10/1977 | Uhlmann et al. | 525/453 |
| 4,686,137 | 8/1987 | Ward, Jr. et al. | 428/290 |

FOREIGN PATENT DOCUMENTS

179916 7/1988 Japan.
2087909 11/1980 United Kingdom.

*Primary Examiner*—Ralph H. Dean
*Attorney, Agent, or Firm*—Timothy J. Troy

[57] ABSTRACT

Novel neopentasiloxane compounds of the general formula $Si[OSiR_2Q]_4$ wherein R denotes a monovalent hydrocarbon or halohydrocarbon group and Q denotes a group R or a group comprising a block of at least two oxyalkylene units and having a terminal group containing a reactive hydrogen atom, not more than one Q denoting an R group. The invention also encompasses a film-forming composition comprising a curable polyurethane resin and the neopentasiloxane, and the use of the film-forming compositions to provide breathable (water vapour permeable) coatings on textile fabrics.

8 Claims, No Drawings

ORGANOSILICON COMPOUNDS AND THEIR USE IN FILM-FORMING COMPOSITIONS

This is a division of application(s) Ser. No. 07/844,090, filed Mar. 2, 1992, now U.S. Pat. No. 5,246,996.

This invention relates to novel organosilicon compounds. It also relates to their use in the preparation of film-forming compositions and the formation of coatings, in particular those which are permeable to water vapour while retaining a high degree of impermeability to liquid water. The invention is particularly concerned with coatings for textile materials, for example those which are useful for the production of the so-called breathable waterproof textiles.

There has always been a demand for waterproof fabrics, especially for fabrics which at the same time are both waterproof and allow the passage of water vapour. Such fabrics find application inter alia in the manufacture of garments and tents exhibiting an improved level of comfort for the user, for example by allowing the passage and escape of water vapour generated by the human body.

Several methods have been proposed to obtain such breathable fabrics. One method comprises the use of tightly woven specialty yarns or yarns made by combining a bulky yarn with a high shrinkage yarn. Another method involves the use of microporous coatings from materials such as polyurethanes or polyvinylchloride which contain micropores of an average diameter below 100 microns, preferably less than 10 microns. These pores do not allow liquid water to pass through but are large enough to allow water vapour molecules to pass through. The use of microporous materials is often combined with the use of a water repellent finish, e.g. based on a silicone polymer. This method is also sometimes combined with the use of a so-called buffer coating which consists of a hydrophilic finish which absorbs excess water vapour and stores it close to the microporous layer to allow its transmission at a later stage. A third method of providing breathable waterproof finishes is the use of non-porous hydrophilic coatings. The basic principle behind this is the incorporation of hydrophilic chemical groups into the chain of the polymers used for the coating. These hydrophilic groups act as stepping stones allowing the water vapour molecules to pass along the chain and through the coating. The coating may thus consist of hard, e.g. polyurethane segments and soft, e.g. polyether segments.

In G.B. application 2 087 909 there is provided a breathable non-porous polyurethane film of a block copolymer formed from a low molecular weight difunctional compound to provide hard segments in the film, a polyethylene glycol to provide soft segments in the film and a diisocyanate. In U.S. Pat. No. 4,686,137 coated textiles are disclosed which are impermeable to liquid water but which have high water vapour permeability, comprising a fabric web and a uniform non-porous coating on at least one surface of the web, the coating comprising a multipolymer which is an essentially linear segmented copolymer chain characterised by at least one polyurethane or polyurethane urea hard segment and a soft block copolymer comprising at least one hydrophilic soft block and one hydrophobic soft block. The hydrophilic component of the soft block may be a polyalkylene oxide. The hydrophobic block may be a polydialkylsiloxane. In Japanese Patent 63/179916 there is provided a thermoplastic polyurethane resin having soft segments of polyols and hard segments of aliphatic diisocyanates and aliphatic diamines. The diols comprise polysiloxane diols and polyoxytetramethylene glycol with a MW of 800 to 2200. In our copending application (Reference MS-P 509) U.S. Pat. No. 672,993 a film-forming copolymer is provided which is formed by the copolymerisation of 100 parts by weight of a curable polyurethane resin and 10 to 100 parts by weight of an organosilicon compound consisting essentially of tetravalent $SiO_2$ units and monovalent $R_3SiO_{\frac{1}{2}}$ and $R'R_2SiO_{\frac{1}{2}}$ units, the ratio of monovalent units to tetravalent units being from 0.4/1 to 2/1 and from 40 to 90% of all monovalent units present in the organosilicon compound being $R'R_2SiO_{\frac{1}{2}}$ units, wherein R denotes a monovalent hydrocarbon group having up to 8 carbon atoms and R' denotes a polyoxyalkylene group which is terminated by a hydroxyl group.

It has been found, however, that many vapour permeable waterproof polyurethane coatings for fabrics suffer from poor abrasion resistance and a reduction in the waterproofing, measured as hydrostatic head, when the breathability or water vapour transmissibility is increased. It is also apparent that no commercially-available breathable waterproof coating materials exist for the textile market which are based on aqueous curable solid non-porous polyurethane resins. We have now found that improved polyurethane coatings can be provided by incorporating therein certain organosilicon compounds. The organosilicon compounds which are useful in these improved coatings are novel materials and are included within the scope of this invention.

According to one aspect of the present invention there is provided a novel organosilicon compound represented by the general formula $Si[OSiR_2Q]_4$ wherein R denotes a monovalent group having from 1 to 8 carbon atoms and free of aliphatic unsaturation selected from hydrocarbon and halogen-substituted hydrocarbon groups and Q denotes a group R or a group comprising a block of at least two oxyalkylene units and having a terminal group containing a reactive hydrogen atom provided that not more than one Q group in the molecule denotes a group R.

By analogy with organic chemistry, the novel organosilicon compound will be referred to in this specification as a neopentasiloxane, whereby is meant the substitution of a central silicon atom with 4 tri-substituted silicon atoms linked to the central silicon atom via Si—O—Si bonds.

Each of the groups R in the neopentasiloxanes of the invention may independently be an alkyl, aryl, alkaryl, aralkyl or a halogen-substituted alkyl, aryl, alkaryl of aralkyl group. Examples of such groups include methyl, ethyl, isopropyl, phenyl, tolyl, phenylethyl or trifluoropropyl. Preferably at least 50% and most preferably at least 80% of all R groups are methyl.

The groups denoted by Q in the general formula of the novel organosilicon compounds of this invention are characterised by having a block of at least two oxyalkylene units and a terminating group containing a reactive hydrogen atom. As the oxyalkylene units there may be present oxyethylene, oxypropylene or oxybutylene units. For optimum water vapour permeability in the polyurethane textile treatment according to this invention none of the Q groups denotes a group R; also at least 85% of the total number of oxyalkylene units are oxyethylene, any remaining oxyalkylene units being oxypropylene. The blocks of oxyalkylene units may be attached to the silicon atom through any suitable chemical group. It may be a divalent hydrocarbon group ($-C_nH_{2n}-$) for example $-(CH_2)_3-$, $-(CH_2)_4-$ or $-CH_2(CH_3)CHCH_2-$ or a divalent hydrocarbon group in which the carbon chain is interrupted by hetero atoms, for example oxygen, nitrogen or sulphur. Preferably the linking group has less than 8 carbon atoms. It is also preferred that the linking groups are attached through a silicon to carbon bond as such bonds are believed to be more hydrolytically stable than, for example, $-Si-O-C-$ linkages. The group terminating Q can be any group containing reactive hydrogen for example carboxyl, hydroxyl, amine or amide but from considerations of availability is preferably hydroxyl. The groups denoted by Q are preferably those represented by the general formula $-C_sH_{2s}[OC_2H_4]_n[OC_3H_6]_mOH$ wherein s is an integer with a value of from 3 to 6, n is an integer having a value of from 5 to 100 and m is zero or an integer having a value of from 1 to 80, wherein $n>m$. The value of s is most preferably 3.

The neopentasiloxanes of the invention in which Q is attached to Si via a SiC linkage can be prepared by reacting in the presence of a hydrosilylation catalyst a neopentasiloxane of the formula $Si[OSiR_2H]_4$ or $Si[OSiR_2H]_3[OSiR_3]$, wherein R is as defined hereinabove, with a polyoxyalkylene compound having a block of at least two oxyalkylene groups, a terminal group having a reactive hydrogen atom and a second terminal group having olefinic unsaturation. The polyoxyalkylene compounds may be, for example that represented by the general formula $CH_2=CH-C_{s-2}H_{2s-4}[OC_2H_4]_n[OC_3H_6]_mOH$, wherein s, n and m are as defined above. Suitable catalysts for the addition of SiH groups to $CH_2=CH-$, the so-called hydrosilylation reaction, are well known in the art and include Pt-containing compounds such as $PtCl_2$ and $H_2PtCl_6$ and complexes of Pt compounds with olefins and organosilicon compounds and polymers having olefinic unsaturation. Preferred polyoxyalkylene compounds are allyl terminated polyethers. Neopentasiloxanes of the formula $Si[OSiR_2H]_4$ are known materials. They may be produced e.g. by reacting tetraethyl orthosilicate with a disiloxane of the general formula $(HR_2Si)_2O$ in the presence of an acidic catalyst. Neopentasiloxanes of the invention in which the groups Q are attached to silicon via an $-Si-OC-$ linkage may be obtained by converting the silicon-bonded hydrogen atom in e.g. $(HR_2SiO)_4Si$ to alkoxy such as methoxy or ethoxy and thereafter reacting the product with a polyoxyalkylene diol. The preparative reactions may be carried out in the presence of any suitable solvent, preferably hydrocarbon solvents such as toluene and xylene and at any appropriate temperature. Conveniently the reaction is carried out at the reflux temperature of the solvent, for example from about 100° C. to about 150° C.

The presence of the reactive terminal group in Q enables the novel neopentasiloxanes to enter into reaction with other compounds and polymers. In particular, certain of the neopentasiloxanes may be reacted with curable polyurethane resins to provide film-forming compositions which can be employed as coating materials for rigid and flexible substrates and for the production of self-supporting films.

In a further aspect, therefore, this invention includes a film-forming composition which comprises 100 parts by weight of a curable polyurethane resin with from 10 to 100 parts by weight of an organosilicon compound represented by the general formula $Si[OSiR_2Q]_4$ wherein R denotes a monovalent group having from 1 to 8 carbon atoms and free of aliphatic unsaturation selected from hydrocarbon and halogen-substituted hydrocarbon groups and Q denotes a group R or a group of the general formula $-C_sH_{2s}[OC_2H_4]_n[OC_3H_6]_m OH$ wherein s is an integer from 3 to 6, n is an integer from 5 to 100 and m is zero or an integer from 1 to 80, provided that $n>m$ and not more than one Q denotes a group R.

The curable polyurethane resin provides the hard segments of the cured polymer film. Operative curable polyurethane resins include both solvent-based and water-based resins and are exemplified by polyether urethanes, polyester urethanes and polyether urethane ureas. The term "curable polyurethane resins" excludes for example the so-called air drying polyurethane systems which are prereacted to such extent that virtually no reactive groups capable of participating in a curing reaction remain on the molecules.

Suitable curable polyurethane resins include those of the so-called two component type. They comprise difunctional molecules which are at most partially reacted with a crosslinking agent leaving some available reactive groups through which further cure or other reaction can occur. Preferably the curable polyurethanes are derived from low molecular weight difunctional compounds including straight or branched chain aliphatic compounds, cyclic compounds and aromatic compounds in which the functional groups are of substantially equal reactivity. Examples of low molecular weight difunctional compounds which can be used include diols such as ethylene glycol, diethylene glycol, triethylene glycol, 1,4-butanediol, thiodiglycol, 2,2,-dimethylpropane-1,3-diol, 1,4-bishydroxymethyl-benzene, bis-hydroxyethyl disulphide, cyclohexane-dimethanol, diamines such as ethylene diamine, dihydrazides such as carbodihydrazide, oxalic hydrazide, hydrazine and substituted hydrazines. By increasing the molecular weight of the difunctional unit the hardness of the segments is reduced. It is therefore preferred to use difunctional compounds for the hard segment which have a molecular weight not greater than 200. The difunctional component may be a single compound or two or more such compounds.

Normally the crosslinking agents for the polyurethane resins are isocyanate or formaldehyde compounds. Examples of suitable crosslinkers are diphenylmethane-4,4-diisocyanate, toluene diisocyanate, hexamethylene-1,6-diisocyanate, 1-isocyanato-3,3,5-trimethyl-5-isocyanatomethyl cyclohexane and melamine formaldehyde. Suitable polyurethane compositions include those which cure by reaction of e.g. polymeric ether glycols and a diisocyanate crosslinker, optionally also including chain extension with diamine or dihydroxy derivatives. By the choice of various types of crosslinkers, e.g. aliphatic or aromatic isocyanates, various types of glycols, e.g. polyoxyethylene, polyoxypropylene or polyoxytetramethylene and various types of chain extenders the structural properties of the polyurethane segment of the copolymer may be varied depending on the end use of the material. Particularly preferred for use in this invention is a polyurethane urea formed from the polymerisation of diphenylmethane diisocyanate, ethylene diamine and polytetramethylene oxide. Curable compositions may also include catalysts which accelerate the curing of the components. Suitable catalysts include organic acids, e.g. p-toluene sulphonic acid. It is preferred that the curable polyurethane resin is provided as a solution or dispersion in a suitable solvent or other diluent, for example dimethyl formamide, water, toluene or ethyl acetate. The content of polyurethane resin in the solution or as dispersion is not critical but is preferably in the range from 35 to 50% by weight.

When at least 70%, and preferably at least 85%, of the oxyalkylene units in Q are oxyethylene the film-forming composition is particularly adapted to the formation of waterproof, breathable coatings on textile fabrics. It has been found that the incorporation of such a neopentasiloxane into the film-forming composition imparts improved water vapour permeability (breathability) to the cured film. For such an application the polyoxyalkylene blocks in each Q preferably have a molecular weight of at least 300, more preferably at least 1000. The higher the molecular weight, especially in the case of the oxyalkylene units being mainly oxyethylene units, the higher will be the water vapour permeability of the cured film. However, too high a molecular weight will tend to reduce the strength and the water-proofing of the film. It is therefore preferred that each polyoxyalkylene block has a molecular weight which does not exceed 4000.

The film-forming composition can be prepared by merely mixing the two components, that is the polyurethane resin and the neopentamer. It may then be converted e.g. at elevated temperature, during subsequent processing to a cured film. It is, however, preferred that the neopentasiloxane is first dissolved in a suitable solvent, e.g. ethyl acetate, toluene, dimethyl formamide or water. The composition should comprise from 10 to 100 parts by weight of the neopentasiloxane per 100 parts by weight of the polyurethane resin. Preferably 18 to 70 parts of the organosilicon compound are used for every 100 parts by weight of the polyurethane resin, most preferably 30 to 45. The chemical reactivity of the polyurethane resin should be sufficient to permit both the cure of the resin and its reaction with the neopentamer. In certain cases, therefore, it may be desirable to increase the amount of crosslinking agent over that normally present in commercially available polyurethane resins. Catalyst levels may also be increased accordingly in order to retain reasonably short crosslinking times. In addition to its catalyst and crosslinking components the polyurethane resin may also comprise solvents, diluents, pigments, fillers, dyes and other materials which are well known and standard ingredients for textile coating compositions.

As hereinbefore stated the film-forming compositions of this invention are particularly suitable for the formation of waterproof, water vapour-permeable coatings on textiles and other porous substrates. The compositions comprising the mixture of polyurethane resin and neopentasiloxane may be applied to the substrate employing any appropriate coating technique, for example by padding, spraying, dipping, direct coating, transfer coating and calendering. The amount of composition applied to the substrate is not narrowly critical and will depend to some extent upon the intended use of the substrate. Conventional levels for waterproof, breathable coatings are in general appropriate, that is sufficient composition should be applied to provide from about 15 to 50 grams of cured composition per square meter of substrate surface. Following application the applied composition is cured. Exposure to temperatures in the range from about 120° C. to about 180° C. for a time of from about 30 seconds to about 4 minutes is normally sufficient to achieve the desired degree of cure. However, times and temperatures outside these ranges may be employed if desired. In common with conventional coating techniques, when the applied composition contains a solvent or other diluent it is preferable to remove at least some of the solvent or diluent by the application of a drying step prior to cure.

The compositions of this invention may be employed to fabricate self-supporting films by conventional techniques. For example the composition may be spread on a substrate, e.g. paper having a non-stick surface, and cured employing temperatures and times indicated herein. The cured film may then be released from the substrate or allowed to remain thereon until required for use. Such films may be employed to provide waterproof, breathable coatings on porous e.g. textile substrates by lamination of the film to the substrate. In another aspect, therefore, this invention provides a method for treating a substrate, particularly a textile substrate, which comprises forming a self-supporting film from a film-forming composition of this invention and thereafter laminating said self-supporting film to said substrate.

Any of a variety of substrates may be treated according to this invention. It is, however, particularly adapted to the production of waterproof, breathable coatings in porous textile fabrics, for example nylon, polyester and polyester cotton for such end applications as waterproof garments, tenting materials, tarpaulins and the like.

The invention will now be illustrated in the following examples in which all parts and percentages are expressed by weight, unless otherwise stated.

Examples 1 to 3

Preparation of suitable organosilicon compounds

To a flask equipped with a dropping funnel, condenser, thermometer and stirrer were charged 284 g (0.128 molar part based on $CH_2=CH-$) of $CH_2=CH-CH_2(OCH_2CH_2)_{50}OH$ and 10 g (0.121 molar part based on SiH) of $Si[OSi(CH_3)_2H]_4$, toluene (100 g) and 0.3 g of sodium acetate. The flask was heated to 90° C. and $2\times10^{-5}$ mole of Pt per mole of SiH were added in the form of chloroplatinic acid. The temperature was raised until the toluene refluxed at about 125° C. and the reaction was continued till all SiH groups had reacted (this was monitored by infrared spectroscopy). The resulting solution was analysed and found to contain the organosilicon neopentamer compound (N1) having the formula

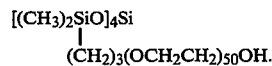

In Examples 2 and 3 the process described above was repeated except for the fact that allylpolyoxyalkylene reactants having respectively 12 (charge weight 75 g) and 32 (charge weight 188 g) oxyethylene groups were used. The resulting neopentamer compounds N2 and N3 had the respective formulae

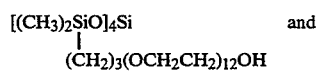

-continued $$[(CH_3)_2SiO]_4Si$$
$$|$$
$$(CH_2)_3(OCH_2CH_2)_{32}OH.$$

Examples 4 to 8

5 compositions were prepared by mixing 100 parts of a polyurethane composition, Larithane B850 provided by Larim SpA, which is a 50% dispersion of an aromatic polyester, two-component polyurethane in a mixture of toluene and methyl ethyl ketone with 7.5 parts of Larithane CL3A which is a 25% solution of melamine formaldehyde resin crosslinker in a $C_4$ alcohol, 1.5 parts of Larithane CT3A which is a 25% solution of p-toluene sulphonic acid catalyst in a $C_4$ alcohol, 3 parts of a matting agent and 12.5, 16.75 and 21.5 parts of the compound N1 respectively for Examples 4, 5 and 6 and 12.5 parts of compounds N2 and N3 respectively for Examples 7 and 8.

A Wiggins Teape 703 plain transfer coating paper was coated with each of the compositions of Examples 4, 7 and 8 by coating a first layer which was dried for 30 seconds at 90° C., heated for 30 seconds at 150° C., coating a second layer, drying for 15 seconds at 90° C. and curing at 150° C. for 2 minutes. The film thickness of the combined coats gave a coating density of 30 g/m². The cured film was then peeled from the backing paper to give Films 4, 7 and 8 and were subjected to breathability testing as described hereinafter. The compositions of Examples 4, 5 and 6 were also coated onto 2 oz nylon fabric according to the same coating method to give Fabrics 4, 5 and 6 which were tested for breathability and water absorption.

Examples 9 to 14

Six compositions were prepared by mixing 100 parts of an aqueous aromatic self-crosslinking polyurethane having 35% solids with 2 parts of a melamine formaldehyde crosslinker having 100% solids, 2 parts of a polyacrylic thickener, 0.2 part of a sulphonic acid catalyst at 25% solids and 1.85, 3.9, 6.2, 8.7, 11.7 and 15 parts of compound N1 respectively for Examples 9 to 14. The compositions were then coated onto 2 oz nylon by the method described for Examples 4 to 6, giving Fabrics 9 to 14.

Comparative Examples C1 to C6

C1 was a composition as given for Example 4 wherein the organosilicon neopentamer compound was omitted;

C2 was a composition as given for Example 4 wherein the organosilicon neopentamer was replaced with an organosilicon compound of the average formula $$[(CH_3)_3SiO_{\frac{1}{2}}]_x[(CH_3)_2SiO_{\frac{1}{2}}]_y[SiO_2]_z$$
$$|$$
$$(CH_2)_3(OCH_2CH_2)_{50}OH$$

wherein the ratio x/y/z has the value 0.7/0.8/1.0;

C3 was a composition as given for Example 4 wherein the organosilicon neopentamer was replaced with an organosilicon compound of the average formula $$[(CH_3)_3SiO_{\frac{1}{2}}]_x[(CH_3)_2SiO_{\frac{1}{2}}]_y[SiO_2]_z$$
$$|$$
$$(CH_2)_3(OCH_2CH_2)_{32}OH$$

wherein the ratio x/y/z has the value 0.7/0.8/1.0;

C4 was a composition as given for Example 4 wherein the organosilicon neopentamer was replaced with an organosilicon compound of the average formula $$[(CH_3)_3SiO_{\frac{1}{2}}]_x[(CH_3)_2SiO_{\frac{1}{2}}]_y[SiO_2]_z$$
$$|$$
$$(CH_2)_3(OCH_2CH_2)_{12}OH$$

wherein the ratio x/y/z has the value 0.7/0.8/1.0;

C5 was a commercially available fabric of a 3-layer laminate with a microporous PTFE film, from W. L. Gore and Associates;

C6 was a commercially available fabric sold under the name Witcoflex 971, believed to be of the type claimed-in G. B. patent specification 2 087 909.

Examples C1 to C4 were made into Films C1 to C4 and Fabrics C1 to C4 according to the method explained in Examples 4 to 8.

Tests

Breathability was tested by filling aluminium cups with a surface area of 54 cm² with 42 g of water and fixing the Fabric or Film over the cup with an adhesive. A plate of Locatex PE18 fabric, which is 100% breathable, was placed over this and the cups were allowed to reach equilibration by placing them on a vibration-free rotating table in an atmosphere of 65% relative humidity (RH) at 20° C. The cups were then weighed accurately and replaced on the rotating table for 24 hours, after which they were weighed again. Two calibration cups covered only with a plate of Locatex PE18 were also weighed accurately and the breathability is calculated as 100× the ratio of the weight loss of the cup with the tested film or fabric over the weight loss of the calibration cup (average of 2). The result of the test are shown in Table I below.

TABLE I

| Example | Breathability (%) | |
|---|---|---|
| | on Film | on Fabric |
| 4 | 88.7 | 60 |
| 5 | — | 73 |
| 6 | — | 82 |
| 7 | 82.0 | — |
| 8 | 79.7 | — |
| 9 | — | 23 |
| 10 | — | 27 |
| 11 | — | 37 |
| 12 | — | 42 |
| 13 | — | 52 |
| 14 | — | 63 |
| C1 | 62.7 | 21 |
| C2 | 81.8 | — |
| C3 | 80.4 | — |
| C4 | 74.0 | — |
| C5 | — | 87 |

The results show that breathability of films made according to the invention is very satisfactory and gives an improvement over the closest prior art. It approaches a commercially available system which uses a very different and expensive technology (Gore-Tex). Breathability on fabrics was lower than for the film, partially because the direct coating method tended to push the coating into the pores of the fabric thus increasing the thickness of the coating in those places. Application by transfer coating. would be expected to lead to improved results.

Hydrostatic head was measured on a Shirley Hydrostatic Head Tester as the height of water column (in cm) required to cause 3 drops of water to penetrate the fabric up to a maximum of 150 cm. This test was carried out on coated fabric both when first coated and after the fabric pieces had been subjected to 5 wash cycles at 40° C. with 50 g of detergent per cycle according to ISO standard 6330-6A. It was also tested after the fabric was subjected to 5000 cycles using a Martindale abrasion tester with a 9 KPa load. The results for those fabrics which were tested are given in Table II.

TABLE II

| Example | Hydrostatic Head (cm) | | |
| --- | --- | --- | --- |
| | Initial | After washes | After abrasion |
| 4 | >150 | >100 | >100 |
| 14 | >150 | >100 | >150 |
| C1 | 150 | 70 | — |

Films of Example 4, 7, 8 and C6 were tested for water absorption. This was done by dissolving 37 g of Tryptone Soy Agar and 1.5f Agar No 2 in 1 liter of hot water, sterilising the solution for 15 minutes at 121° C. and pouring it into culture dishes to allow it to set. This provided a medium for the polyurethane films to absorb water without retaining any on the surface of the films. After 24 hours the films were weighed again and the percentage increase in weight calculated. The test results given in Table III show that the increased hydrophilic nature of the films did not lead to an increased tendency for the films to absorb water.

TABLE III

| Example | % Weight increase due to water absorption |
| --- | --- |
| 4 | 12 |
| 5 | 19 |
| 6 | 11 |
| C1 | 7 |
| C6 | 31 |

That which is claimed is:

1. An organosilicon compound represented by the general formula $Si[OSiR_2Q]_4$ wherein R denotes a monovalent group having from 1 to 8 carbon atoms and free of aliphatic unsaturation, selected from hydrocarbon and halogen-substituted hydrocarbon groups and Q denotes a group R or a group comprising a block of at least two oxyalkylene units and having a terminal group containing a reactive hydrogen atom, provided that not more than one Q group in the molecule denotes an R group.

2. An organosilicon compound as claimed in claim 1 wherein at least 80% of the R groups are methyl.

3. An organosilicon compound as claimed in claim 1 wherein the groups Q have the general formula $-C_sH_{2s}[OC_2H_4]_n[OC_3H_6]_mOH$, wherein s is an integer of from 3 to 6 inclusive, n is an integer of from 5 to 100 inclusive and m is zero or an integer of from 1 to 80 inclusive, n having a value greater than m.

4. An organosilicon compound as claimed in claim 3 wherein at least 85% of the oxyalkylene units in Q are oxyethylene units, any remaining oxyalkylene units being oxypropylene.

5. A method of treating a substrate which comprises applying thereto a film-forming resin which comprises 100 parts by weight of a curable polyurethane resin and from 10 to 100 parts by weight of an organosilicon compound represented by the general formula $Si[OSiR_2Q]_4$ wherein R denotes a monovalent group having from 1 to 8 carbon atoms and free of aliphatic unsaturation, selected from hydrocarbon and halogen-substituted hydrocarbon groups and Q denotes a group R or a group of the general formula $-C_sH_{2s}[OC_2H_4]_n[OC_3H_6]_mOH$, wherein s is an integer of from 3 to 6, n is an integer of from 5 to 100 and m is zero or an integer of from 1 to 80, provided that n>m, and that no more than one Q group denotes a group R, and curing the applied composition.

6. A method of treating a substrate which comprises forming a self-supporting film from a film-forming resin which comprises 100 parts by weight of a curable polyurethane resin and from 10 to 100 parts by weight of an organosilicon compound represented by the general formula $Si[OSiR_2Q]_4$ wherein R denotes a monovalent group having from 1 to 8 carbon atoms and free of aliphatic unsaturation, selected from hydrocarbon and halogen-substituted hydrocarbon groups and Q denotes a group R or a group of the general formula $-C_sH_{2s}[OC_2H_4]_n[OC_3H_6]_mOH$, wherein s is an integer of from 3 to 6, n is an integer of from 5 to 100 and m is zero or an integer of from 1 to 80, provided that n>m and that no more than one Q group denotes a group R, and thereafter laminating said film to said substrate.

7. A method as claimed in claim 5, wherein the substrate is a textile fabric.

8. A method as claimed in claim 6, wherein the substrate is a textile fabric.

* * * * *